(12) United States Patent
Sinibaldi et al.

(10) Patent No.: US 11,529,161 B2
(45) Date of Patent: Dec. 20, 2022

(54) ADAPTATIVELY MORPHING SURGICAL GRASPER

(71) Applicant: FONDAZIONE ISTITUTO ITALIANO DI TECNOLOGIA, Genoa (IT)

(72) Inventors: Edoardo Sinibaldi, Pontedera (IT); Yu Huan, Pontedera (IT); Arianna Menciassi, Pontedera (IT); Barbara Mazzolai, Pontedera (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 324 days.

(21) Appl. No.: 16/962,905

(22) PCT Filed: Jan. 25, 2019

(86) PCT No.: PCT/IB2019/050621
§ 371 (c)(1),
(2) Date: Jul. 17, 2020

(87) PCT Pub. No.: WO2019/155316
PCT Pub. Date: Aug. 15, 2018

(65) Prior Publication Data
US 2021/0059701 A1 Mar. 4, 2021

(30) Foreign Application Priority Data

Feb. 6, 2018 (IT) .......................... 102018000002432

(51) Int. Cl.
*A61B 17/29* (2006.01)
*A61B 17/00* (2006.01)

(52) U.S. Cl.
CPC .... *A61B 17/29* (2013.01); *A61B 2017/00876* (2013.01); *A61B 2017/2945* (2013.01)

(58) Field of Classification Search
CPC ......... A61B 17/02; A61B 17/29; A61B 17/30; A61B 2017/0206; A61B 2017/2926;
(Continued)

(56) References Cited

U.S. PATENT DOCUMENTS 5,236,437 A * 8/1993 Wilk .................. A61B 17/29
604/908
5,425,705 A * 6/1995 Evard .............. A61B 17/06061
604/36

(Continued)

FOREIGN PATENT DOCUMENTS

| DE | 10031773 A1 | 11/2001 |
|----|-------------|---------|
| WO | 2013152019 A1 | 10/2013 |
| WO | 2016056908 A1 | 4/2016 |

OTHER PUBLICATIONS

International Search Report and Written Opinion for Corresponding International Application No. PCT/IB2019/050621 (9 Pages) (Apr. 18, 2019).

*Primary Examiner* — Sarah W Aleman
(74) *Attorney, Agent, or Firm* — Lucas & Mercanti, LLP

(57) ABSTRACT

A grasper device for mini-invasive surgery procedures is provided, having two jaws, each of which having two elastically-deformable elements fixed one another and developing according to a main longitudinal direction, in particular a front element which contacts the tissue to be grasped and a back support element receiving a grasping force from a proximal command and having a higher modulus of elasticity than the front element. During the application of a grasping force $F_z$, the two elements deform along a transverse direction that is orthogonal to the main longitudinal direction and to the grasping force $F_z$.

19 Claims, 9 Drawing Sheets

(58) Field of Classification Search
CPC .... A61B 2017/2932; A61B 2017/2945; A61B 18/1442; A61B 18/1445
See application file for complete search history.

(56) References Cited

U.S. PATENT DOCUMENTS

| | | | | |
|---|---|---|---|---|
| 5,921,996 | A * | 7/1999 | Sherman | A61B 17/122 606/157 |
| 6,036,706 | A * | 3/2000 | Morejohn | A61B 17/122 606/157 |
| 6,616,683 | B1 * | 9/2003 | Toth | A61B 17/29 606/205 |
| 2017/0348044 | A1 * | 12/2017 | Wang | A61B 17/295 |
| 2018/0042613 | A1 * | 2/2018 | Gerosolimo | A61B 17/122 |

* cited by examiner

ADAPTATIVELY MORPHING SURGICAL GRASPER

CROSS-REFERENCE TO RELATED APPLICATIONS

This application is a 371 of PCT/IB2019/050621, filed Jan. 25, 2019, which claims the benefit of Italian Patent Application No. 102018000002432, filed Feb. 6, 2018.

TECHNICAL FIELD

The present invention relates to mechanical end-effectors, in particular to a miniaturized grasper or retractor devised to grasp or retract soft tissue during Minimally Invasive Surgery (MIS) procedures.

BACKGROUND

Minimally Invasive Surgery (MIS) is a growing field of technology aimed at reducing the negative effects upon patients of traditional open-surgery procedures, such as scars, infections, patient discomfort and long recovery times.

Known techniques of MIS employ tools, which may be manually or robotically controlled, to manipulate tissues. Typically, MIS procedures are carried out by inserting, through an already existing orifice or through incisions having dimensions ranging from few millimetres to centimetres, a tethered tool into the surgical site of interest. MIS tools are similar to those employed in conventional open-surgery, except that their end-effectors, i.e. the working extremities, are connected to a handle by means of a surgical support shaft. In such a way, a surgeon can manipulate the end-effector of the tool from outside the patient's body, limiting the impact of non-interested areas.

Generally speaking, dealing with MIS end-effectors implies taking into consideration the size/operation constraints arising from the necessity of inserting such tools through small openings in the patient's body, in particular by using guiding cannulas or catheters.

In addition, a compromise need to be achieved between the need for applying an appropriate level of grasping/manipulation force and the avoidance of any damage to the manipulated tissue. In particular, on the one hand, during surgical procedures it is essential achieving an effective interaction between the end-effector, in particular a grasper, and the tissue in order to firmly clutch, hold or retract the latter, and therefore a sufficiently-high grasping force is required. On the other hand, and with reference to FIG. 1, whenever tissue holding or manipulation requires an increase in the grasping force (F), this directly translates into an increase in the stress ($\sigma$) induced on the tissue, with potential damage as soon as a certain stress threshold ($\sigma_{max}$) is exceeded. For the sake of simplicity, assuming to be in a linear elastic regime, the safe working region is the blank region shown in FIG. 1: the maximum allowed stress poses an upper bound ($F_{max}$) on the grasping force that can be exerted, thus limiting tool operation. Therefore, the interaction between the grasper and the tissue should also be safe enough in order to ensure that the induced stress on the tissue is within its safety threshold, thus preventing significant damage or trauma.

However, the prior art does not provide an effective compromise between the aforementioned opposite needs.

WO2013/152019 discloses a compliant grasper that grasps tissue using a jaw made completely from a monolithic compliant member. The jaw has opposite grasping arms that deform longitudinally, i.e. along the main direction of development of an elongated housing member the grasper is attached to. However, jaw deformation along the longitudinal direction entails an increase of the tooltip length, thus posing limitation on the workspace and tool operability. Moreover, longer deformable tooltips are intrinsically less effective towards their distal end because of basic mechanical effects.

WO2016/056908 discloses a mechanical end-effector, in form of a grasper, that provides the user with a feedback about the forces that, through the grasper, are applied to the tissue. The grasper comprises two movable parts applied at the end of bendable supports. When a force applied to the bendable supports exceeds a predefined value, they flex, moving apart the movable parts. Also in this case, the tool does not allow an optimal and firm retaining of the grasped tissue.

SUMMARY OF THE INVENTION

The technical problem posed and solved by the present invention is to overcome one or more of the drawbacks previously mentioned with reference to the known art.

Such a problem is solved by a grasper device for MIS procedures according to claim 1.

Preferred features of the present invention are the object of the dependent claims.

Protection may be sought also for a single jaw of said grasper device as defined in claim 1 and/or in the dependent claims.

As used herein, the term "grasper", or "grasper device", denotes an end-effector, in particular for MIS procedures, which is capable of exerting a grasping—or catching, drawing—action, upon a biological tissue or, generally speaking, an item to be manipulated. The grasper can be incorporated as part of a surgical tool providing specific (additional) functions, and can be in particular a retractor.

Generally speaking, the grasper of the invention is a miniaturised end-tool, meaning that its dimensions are confined in a range of about 8-15 mm.

The grasper device of the present invention is configured to be attached, removably or fixedly, to a surgical supporting element, in particular to a shaft, developing along a main longitudinal direction.

The grasper has two jaws each of which comprises an elastically-deformable front element, that, in operation, is in contact with an item to be grasped, and an elastically-deformable back support element, fixedly coupled with the front element and configured to receive a grasping force and to transmit it to the respective front element. According to the invention, the front element is more elastically-deformable, i.e. it has a lower modulus of elasticity, than the support element.

According to preferred embodiments, the front element is made of a silicon rubber material and has 100% (elastic) modulus comprised in a range of 0.1-1 MPa. In particular, the front element can be made of a material known as Dragon Skin®.

Preferably, the support element is made of thermoplastic materials with Young (elastic) modulus ranging from 1 GPa to 5 GPa, or alternatively made of super-elastic nitinol alloys (NiTi) with an average Young modulus around 60 GPa.

Generally speaking, the support element can have a modulus of elasticity roughly 10000-100000 times higher than the front element.

In preferred embodiments, the support element can be made of super-elastic Nitinol (NiTi) alloys or of polycarbonate.

In preferred embodiments, each jaw, as well as its front and support element, develops in a main longitudinal direction.

Preferably, the front element and the support element are fixed one another along respective longitudinal edge portions, so as to define a tubular hollow structure therebetween having one or more longitudinal passages or holes.

In operation, the two jaws close one towards the other to grasp the tissue according to a closing, or grasping, direction, in particular a direction which is orthogonal to the longitudinal direction.

The front and support element of each jaw deform according to a transverse direction which is orthogonal to the grasping direction and which is preferably orthogonal to the longitudinal direction.

The proposed configuration allows obtaining an adaptive deformation, or morphing, of each jaw of the device. This result is achieved also by virtue of the different elastic deformability of the front and support element.

Therefore, the overall arrangement is such that when a grasping force is applied to the support element it deforms and transmits such force to the front element that, in turn, deforms. In particular, the front element and the support element deform in a main deforming direction that is orthogonal with respect to the grasping force and, preferably, also with respect to the main longitudinal direction of development of the elements themselves.

The grasper device according to the invention allows achieving simultaneously an effective and safe tool-tissue interaction without increasing the tool cross-section and without introducing size constraints upon the tool workspace.

In particular, in the present invention, by design the contact area or region between grasper and tissue—as associated with the grasper transverse direction—adaptively increases with the grasping force in such a way that a firm retention is provided without damaging the tissue.

In other words, the deformation of the support element and the front element, as responsive to an increasing grasping force, determines an increase in the contact area between the front element and the tissue. Consequently, the increasing grasping force applied by the surgical tool is redistributed over a larger tissue contact area, so that the admissible stress threshold is not overcome or it is reached for higher levels of grasping force with respect to the prior art devices.

Moreover, being the adaptive increase of the contact area orthogonal with respect to the main direction of development of the jaw and the surgical support shaft, no size constraints on the tool workspace and operability are posed. Therefore, a more compact design is allowed.

In addition, transversal morphing allows achieving an even more effective tool-tissue interaction towards the distal portion of the tooltip.

Another advantage of the present invention is that the underlying mechanical action of the miniaturised grasper device, i.e. its adaptive deformation, is intrinsically passive: additional mechanisms, related actuation units or sensors to trigger them are not needed.

Furthermore, the grasper device according to this invention can advantageously be applied to robotic effectors (e.g. the da Vinci tools, devised for teleoperation) as well as to non-robotic effectors (e.g. "traditional" laparoscopic tools, devised for direct manual operation).

It will also be appreciated that the design of the proposed grasper affects the tip of the main tool only: there is no need of extra assistant tools (also needing extra incisions). This also promotes tool dexterity: the proposed technical solution can be implemented, e.g., on top of highly articulated robotic effectors.

Moreover, the proposed tooltip morphing principle and structure can be integrated into generic manipulators: hence, it could be extended to those application fields wherein a grasping action which is both safe for the object and effective/reliable for the operator is sought, including handling of fragile/valuable materials, such as for example glass or food.

Additional features and advantages of the various aspects of the present invention will become apparent from the following detailed description of its preferred embodiments, taken in conjunction with the accompanying figures. Preferred embodiments are intended to explain and exemplify certain aspects of the present of invention, but should not be construed as limiting its scope of protection.

BRIEF DESCRIPTION OF THE DRAWINGS

The present invention and the following detailed description of preferred embodiments thereof may be understood by reference to the following figures.

DETAILED DESCRIPTION OF PREFERRED EMBODIMENTS

In the following, several embodiments of the invention will be described. It is intended that the features of the various embodiments can be combined, where compatible. In general, subsequent embodiments will be disclosed only with respect to the differences with the previously-described ones.

Figure 2:
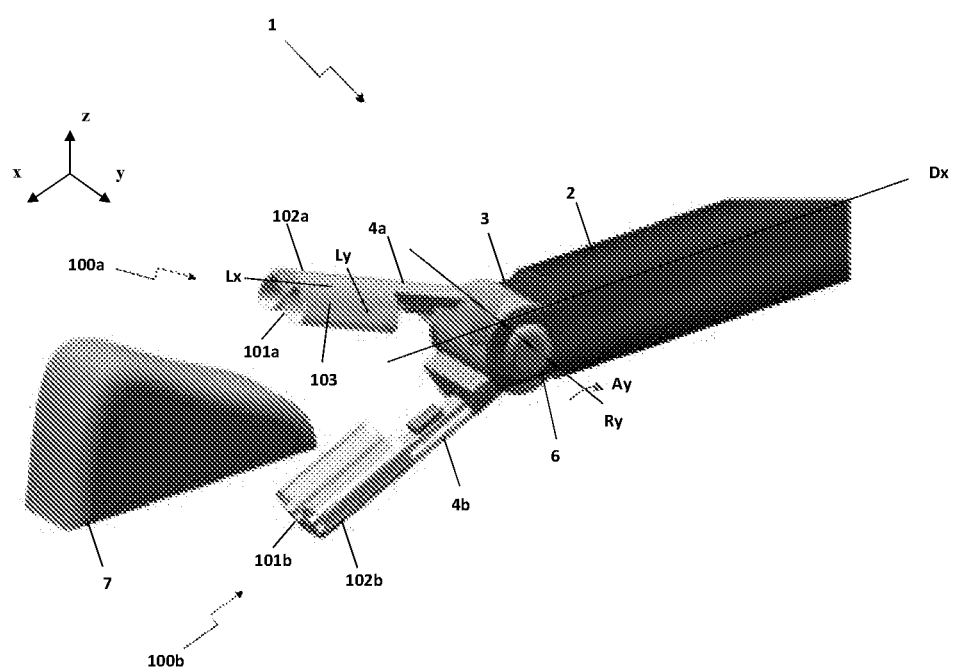
FIG. 2 shows a perspective view of a surgical assembly including a miniaturized grasper device according to a first exemplary first embodiment of the invention.

With reference to FIG. 2, a grasper device, or grasper, according to a preferred exemplary embodiment of the invention is globally denoted by 1. Grasper 1 is configured to be affixed to a support shaft 2 of a main surgical tool. Grasper device 1 mainly comprises a first jaw 100a and a second jaw 100b, which can have the same structure and configuration and which are rotatably coupled at a joint 6.

For better clarity, in the following directions will be defined in conjunction with reference systems (x, y, z) fixed with device jaws 100a, 100b. In FIG. 2, one of such system is represented schematically.

Shaft 2 develops along a main longitudinal direction $D_x$, which is represented in FIG. 2 as mainly parallel to the x axis.

Jaws 100a and 100b are rotatably coupled according to a transverse rotation axis $R_y$, the latter being parallel to the y axis and orthogonal to longitudinal direction $D_x$. Therefore, jaws 100a and 100b close towards each other according to a closing direction, denoted by arrow $A_y$, which is mainly parallel to the z axis.

Grasper device 1 also includes a pulley 3, or a different force/motion transmission means, for actuating the device by means of a proximal command (not shown), e.g., a traditional wire actuation as for the da Vinci surgery system, EndoWrist tools® as disclosed in U.S. Pat. No. 5,792,135A.

Grasper device 1 comprises as well rigid connecting sections 4a and 4b between the rotational joints 6 and respective jaws 100a and 100b.

Each jaw 100a, 100b includes a front element 101a, 101b that, in operation, is in contact with an item 7, generally organic tissue, to be grasped. Front elements 101a, 101b of the two jaws face each other and grasp object 7 therebetween.

Each jaw 100a, 100b also comprises a back support element 102a, 102b configured to receive a grasping force which is exerted distally by the operator through a distal command and transmitted to support element 102a, 102b though pulley 3 as grasping force $F_z$, i.e. a force in the mutual closing direction of jaws 100a, 100b. Both the front element 101a, 101b and the support element 102a, 102b develop according to a main longitudinal direction $L_x$, parallel to the x axis, and to a secondary transversal direction $L_y$, parallel to the y axis.

As it will be explained in more detail with reference to the specific embodiments of the other figures, each front element 101a, 101b and the respective support element 102a, 102b are tightly coupled together. In particular, each front element 101a, 101b and the respective support element 102a, 102b are fixed one another along respective longitudinal edge portions so as to define a tubular hollow structure therebetween.

According to the invention, front element 101a, 101b and support element 102a, 102b are elastically-deformable. In particular, front element 101a, 101b is more compliant than support element 102a, 102b.

The overall arrangement is such that, by virtue of the proposed configuration—in particular of material continuity and compliance—when a grasping force $F_z$ is applied along the z axis to a support element 102a, 102b, the latter deforms consistently, in particular through a displacement along the y axis. The grasping force is as well transmitted to the respective front element 101a, 101b that, in turn, deforms along the y axis.

Figure 1:
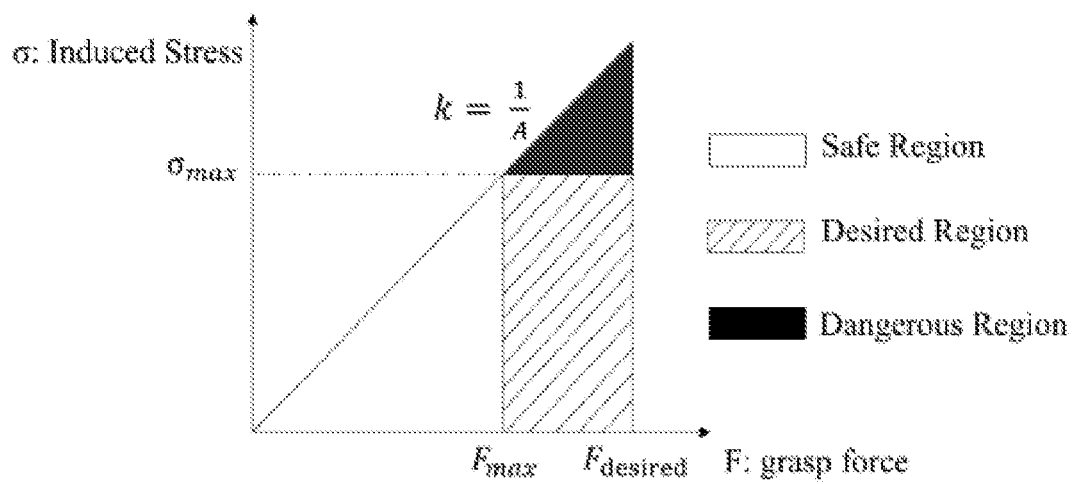
FIG. 1 (formerly introduced with reference to the prior art) is a diagram showing a MIS tool working regions in terms of grasping force and corresponding induced stress.
Figure 3:
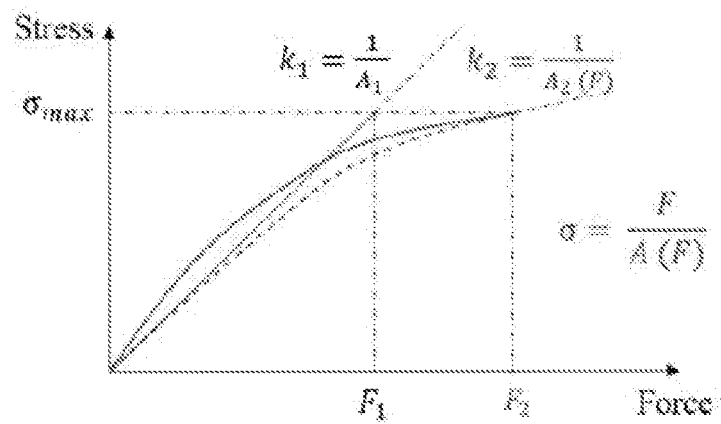
FIG. 3 is a diagram illustrating the working principle of embodiments of the invention in terms of grasping force and corresponding stress applied to a tissue.

Grasping with the grasper device of the present invention is effective and safe since, by design, the contact area between each front element 101a, 101b and the object/tissue 7 adaptively increases with the grasping force in such a way that a firm retention is provided without damaging the tissue. In other words, the deformation of the support element and of the front element, as response to the grasping force, determines an increase in the contact area between the front element and the tissue. Consequently, the force applied to the tissue is redistributed over a larger contact area so that the stress threshold is not overcome or overcome at higher force level with respect to the prior art devices. FIG. 3 illustrates a graph showing the relation between the grasping force F as applied to a support element 102a, 102b and the associated induced stress (σ) upon the object/tissue. A denotes the contact area A between a front element 101a, 101b and the tissue 7, which increases ($A_2 > A_1$) with an increasing grasping force ($F_2 > F_1$).

Preferably, the jaw of the grasper according to the invention has, in cross-section, a symmetrical structure according to the z axis.

According to preferred embodiments of the invention, the grasper device can handle grasping forces $F_z$ up to about 20 N in case of specific tissues to be manipulated, such as liver. According to preferred embodiments, deformation, or morphing, of the grasper jaw incrementally occurs during the application of the grasping force $F_z$ (i.e., up to its maximum considered value).

Figure 4A:
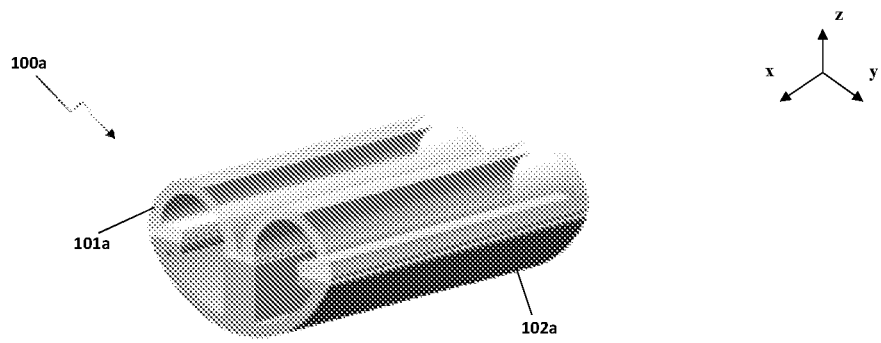
FIG. 4a is a perspective view of a jaw of a miniaturized grasper device according to a second embodiment of the invention.
Figure 4B:
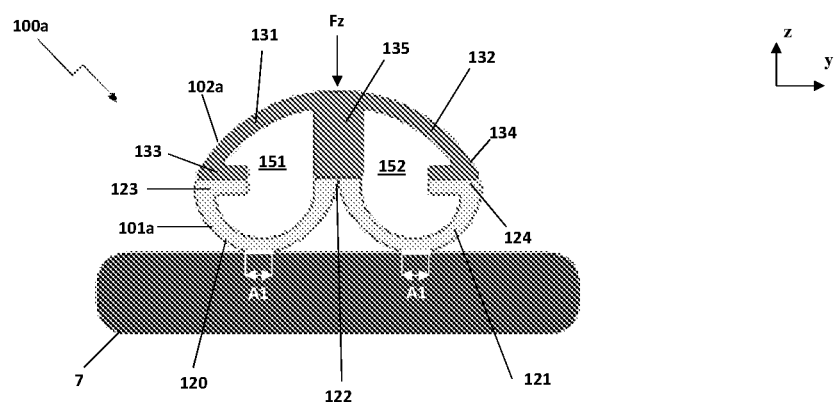
FIG. 4b is a schematic cross-section of a jaw of the miniaturized grasper device shown in FIG. 4a in an "unloaded" configuration.
Figure 4C:
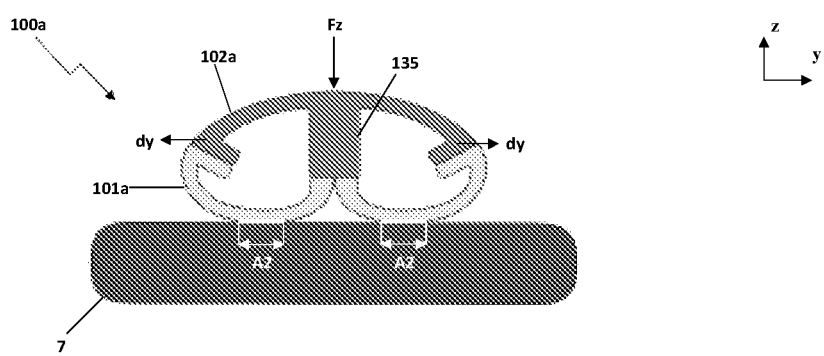
FIG. 4c is a schematic cross-section of a jaw of the miniaturized grasper device shown in FIG. 4a in a "bent", or deformed, configuration.

FIGS. 4a-4c refer to a specific embodiment of the present invention and show in greater detail the structural features of one of the jaws. For the sake of simplicity, for this embodiment and for the following ones only a first jaw will be described. It is intended that the same features apply also to the contralateral second jaw. Still for the sake of simplicity, for the present embodiment the same reference numerals already introduced in conjunction with the exemplary embodiment of FIG. 2 will be used.

Jaw 100a includes a front element 101a and a support element 102a. Both elements have a curved profile and, in the present example, define a jaw which, in cross-section, is substantially shaped as an inverted "ω" closed at the middle or an overall heart shape. Therefore, jaw 100a has a general tubular configuration, with two longitudinal rooms or spaces 151 and 152 extending therethrough.

Preferably, each element 101a, 102a, is shaped, in cross-section, as a double arch.

In particular, front element 101a can be shaped substantially as an "ω". In other words, front element 101a has a substantially bilobed or "lowercase omega" profile. It has two lobes or coves 120, 121, preferably symmetric, arranged side by side. Thus, an end of a lobe is conjunct with an end of the other lobe at an intermediate region 122. The two lateral free ends of lobes 120 and 121 terminate with a lateral abutment or bracket 123, 124 protruding, along the y axis, inwardly with respect to the space subtended by each lobe 120, 121. Preferably, such lateral abutments 123 and 124 are substantially flat in the longitudinal direction x.

Support element 102a is defined by two arched sections 131, 132, in particular defining a continuous arched profile with a single radius of curvature. Support element 102a has at a central, or intermediate, rib 135 protruding, along the z axis, inwardly with respect to the space subtended by the arched profile, substantially centrally with respect to the circumferential development of the arched profile. Each of the two opposite ends of the arched profile terminates with a lateral abutment or bracket 133, 134 protruding, along the y axis, inwardly with respect to the space subtended by the arches. Preferably such lateral abutments 133 and 134 are substantially flat in the longitudinal direction x.

Front element 101a and support element 102a are fixed one another along the respective lateral abutments 123, 133 and 124, 134, representing their longitudinal edge portions. In addition, elements 101a and 102a are coupled together in correspondence of rib 135 and corresponding region 122.

FIGS. 4b and 4c also depict schematically the contact area $A_1$ and $A_2$, respectively, between front element 101a and object/tissue being grasped. In particular, FIGS. 4b and 4c show an unloaded and a bent, or deformed, configuration, respectively, of the jaw 100a.

As shown in FIG. 4c, in presence of grasping force $F_z$, support element 102a and front element 101a adaptively deform along the transversal direction y (displacement $d_y$), so that the contact area A between the front element 101a and the item 7 increases ($A_2 > A_1$). A further increase in $F_z$ would induce a further increase in the contact area A, up to a limit configuration. Thus, grasping force $F_z$ is effectively transmitted to item 7, but the resulting mechanical stresses distribute over an extended contact area $A_2$.

Then, upon removal of the grasping force $F_z$, each jaw 100a and 100b goes back to its original "unloaded" configuration thanks to its elastic behaviour.

Figure 5A:
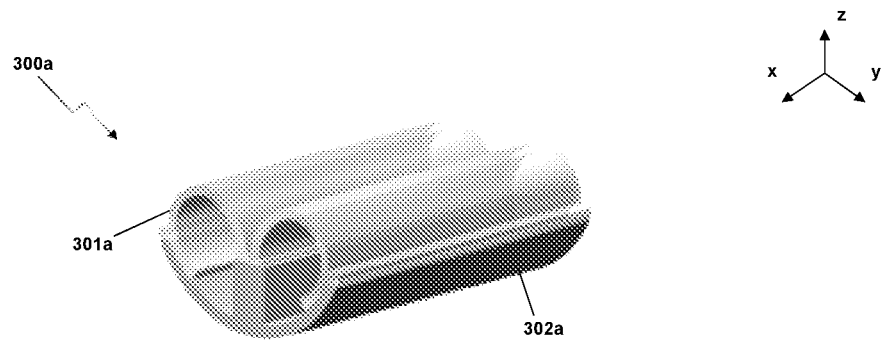
FIG. 5a is a perspective view of a jaw of a miniaturized grasper device according to a third embodiment of the invention.
Figure 5B:
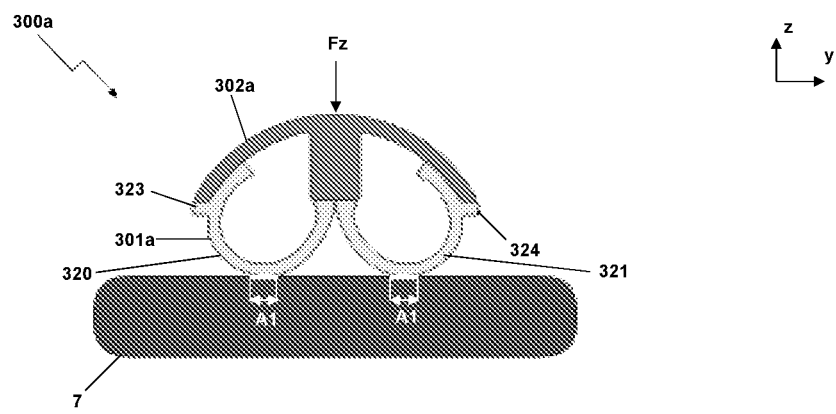
FIG. 5b is a schematic cross-section of a jaw of the miniaturized grasper device shown in FIG. 5a in an "unloaded" configuration.
Figure 5C:
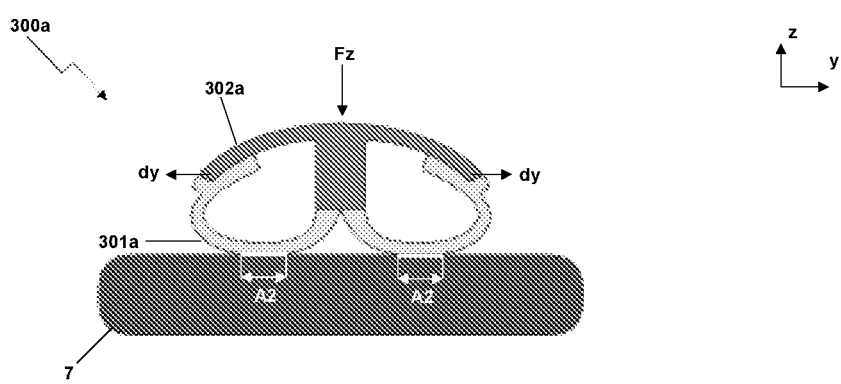
FIG. 5c is a schematic cross-section of a jaw of the miniaturized grasper device shown in FIG. 5a in a "bent", or deformed, configuration.

FIGS. 5a-5c refer to another embodiment of the present invention and show a jaw denoted by 300a. This embodiment differs from the former one as regards the coupling interface between the front element, herein denoted by 301a, and the support element, denoted by 302a.

In particular, front element 301a has rounded lobes 320 and 321. From each of them, at an intermediate position, a short lateral abutment or bracket 323, 324, protrude along the y axis, outwardly with respect to the space subtended by the lobe.

The two opposite ends of the support element 302a have no abutments and lean each upon a respective lateral abutment 323, 324 of front element 301a and externally upon a terminal portion of the respective lobe 320, 321. In cross-section, the considered interface lies substantially along the y axis for the embodiment of FIG. 4a, whereas it also has a component along the z axis for the present one. Accordingly, a different stress distribution exists between the two embodiments at the coupling interface.

Figure 6A:
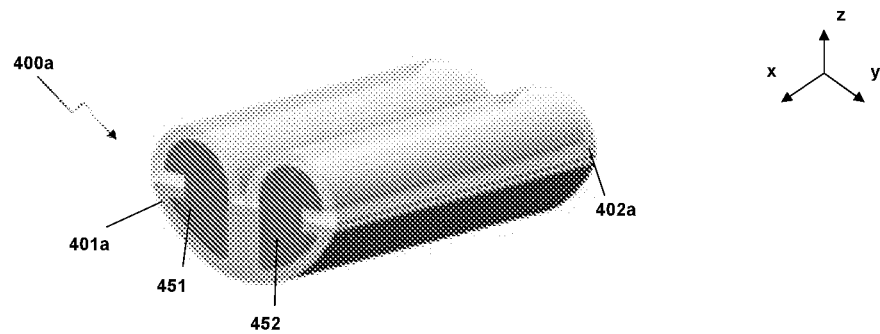
FIG. 6a is a perspective view of a jaw of a miniaturized grasper device according to a fourth embodiment of the invention.
Figure 6B:
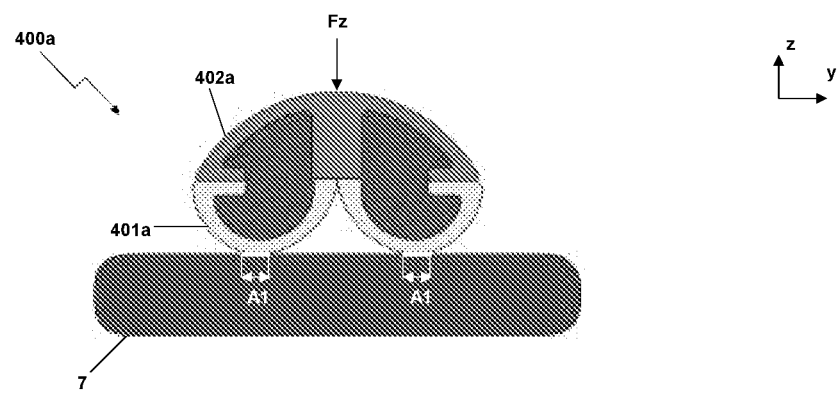
FIG. 6b is a schematic cross-section of a jaw of the miniaturized grasper device shown in FIG. 6a in an "unloaded" configuration.
Figure 6C:
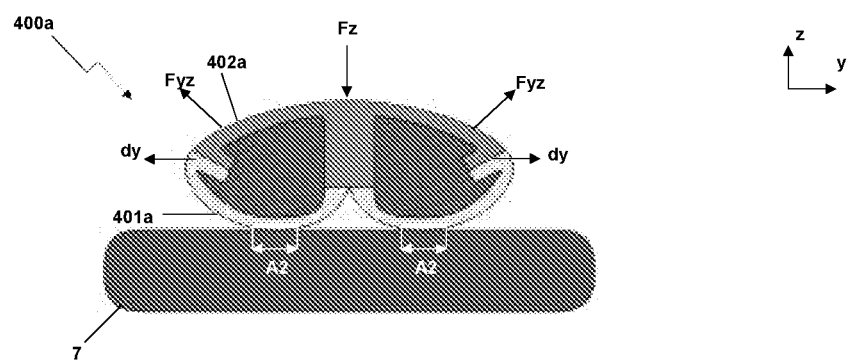
FIG. 6c is a schematic cross-section of a jaw of the miniaturized grasper device shown in FIG. 6a in a "bent", or deformed, configuration.

FIGS. 6a-6c refer to a further embodiment of the present invention and show a jaw denoted by 400a. This embodiment differs from the one of FIG. 4a in that spaces 151 and 152 each house a respective elastically-compressible filler 451, 452. Each filler 451, 452 closely follows the profile of the corresponding space 151, 152 it occupies. Each filler 451, 452 is made of incompressible material, preferably an elastomer (yet a biocompatible liquid could be alternatively considered).

In such case, the deformation of the front element, here denoted by 401a, and the support element, denoted by 402a, along the y axis is fostered by the contact action exchanged with the filler 451, 452, denoted by $F_{yz}$ for the back support in FIG. 6c.

The use of a filler contributes to avoid stress concentrations at the contact interface.

Figure 7A:
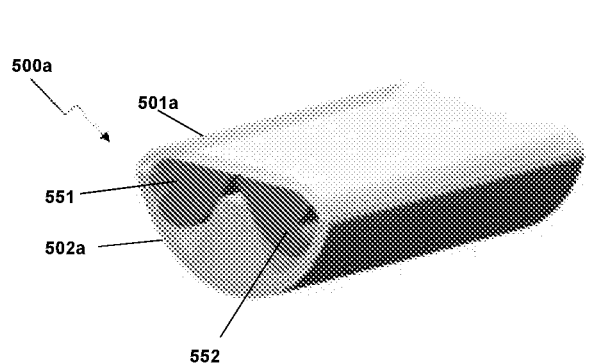
FIG. 7a is a perspective view of a jaw of a miniaturized grasper device according to a fifth embodiment of the invention.
Figure 7A:
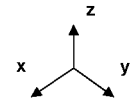
Figure 7B:
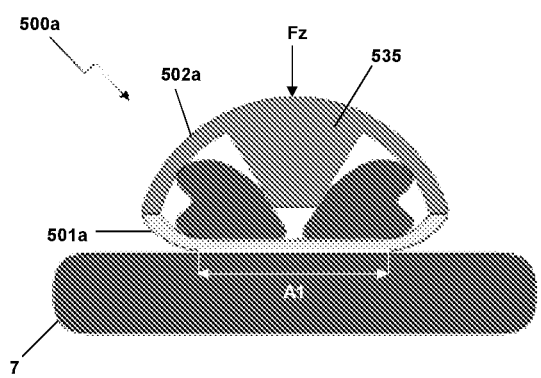
FIG. 7b is a schematic cross-section of a jaw of the miniaturized grasper device shown in FIG. 7a in an "unloaded" configuration.
Figure 7B:
Figure 7C:
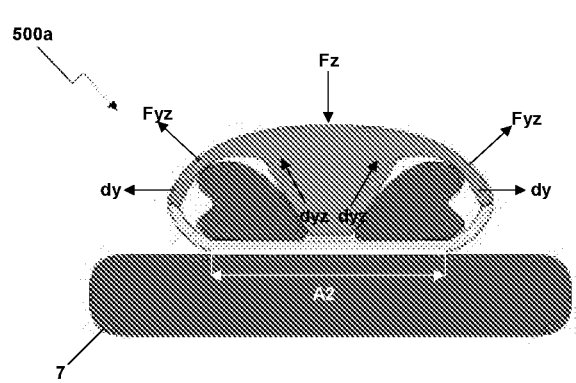
FIG. 7c is a schematic cross-section of a jaw of the miniaturized grasper device shown in FIG. 7a in a "bent", or deformed, configuration.
Figure 7C:

FIGS. 7a-7c depict another embodiment of the present invention and show a jaw denoted by 500a. Also this embodiment provides two fillers, denoted by 551 and 552. The present exemplary grasper device differs from that of FIG. 4a mainly for the shape and configuration of the front element, herein denoted by 501a, and partly for that of the support element, denoted by 502a.

Support element 502a has a curved profile, preferably an arched profile. Support element 502a comprises a rib 535 that protrudes, along the z axis, inwardly with respect to the space subtended by the arch. Preferably, rib 535 has a tapered cross section, in particular wedge-shaped, gradually narrowing towards front element 501a, and is preferably is positioned in the middle or central portion of the arched profile of support element 502a.

Front element 501a has a curved profile, preferably an arched profile, most preferably with a radius of curvature higher than that of support element 502a.

Front element 501a and support element 502a are fixed one another along respective ends of the arches, i.e. along their longitudinal edge portions. In the present embodiment, jaw 500a has a single longitudinal room or space. Said differently, in this case the two inner rooms or spaces are in communication. Inside such spaces, two shaped elastically-compressible fillers 551 and 552 are housed. Fillers 551 and 552 are configured as sliding members.

Each sliding element 551, 552 is located on one side of rib 535, laying on the front element 501a and being constantly in contact with the arched profile of support element 502a. Preferably, each filler 551, 552 has a heart-shape cross-section, narrowing towards central rib 535 and terminating therein with a pointed end.

Grasping force $F_z$, along the z axis, induces support element 502a to deform along the y axis, thus making rib 535 pushing apart sliding elements 551 and 552 (displacement $d_{yz}$). Deformation of support element 502a is also fostered by the contact action $F_{yz}$ exchanged with sliding elements 551 and 552. Thus, the deformation of the support element 502a combined with the movement of the sliding elements 551 and 552 induces the deformation, along the y axis, of front element 501a.

Embodiments shown in FIGS. 8a to 10c encompass permanent magnets, or other magnetic elements, housed at the front element and the support element. As a result of the deformation of the front element and support element, due to the application of the grasping force $F_z$ along the z axis, the magnets relative position changes so that repulsive forces between facing magnet poles are induced, which produce a mechanical action $F_{yz}$, fostering support element deformation. This fostering contribution is passively obtained based on the deformation, thus no additional actuation is required.

Figure 8A:
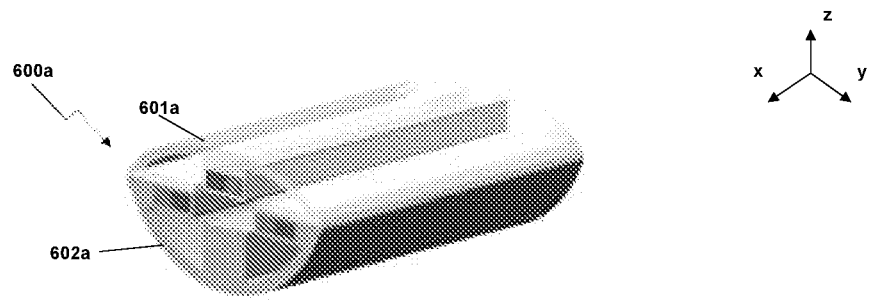
FIG. 8a is a perspective view of a jaw of a miniaturized grasper device according to a sixth embodiment of the invention.
Figure 8B:
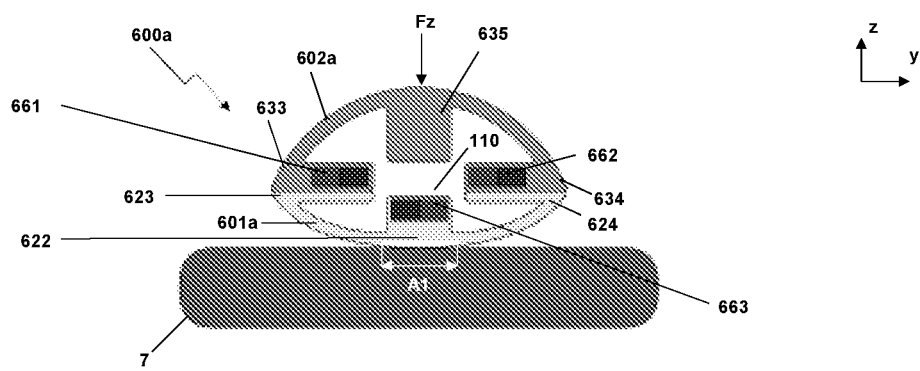
FIG. 8b is a schematic cross-section of a jaw of the miniaturized grasper device shown in FIG. 8a in an "unloaded" configuration.
Figure 8C:
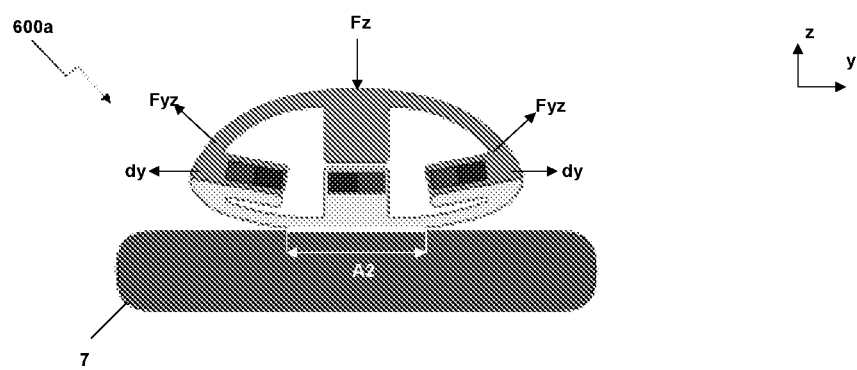
FIG. 8c is a schematic cross-section of a jaw of the miniaturized grasper device shown in FIG. 8a in a "bent", or deformed, configuration.

FIGS. 8a-8c depict an embodiment of the present invention and show a jaw denoted by 600a. Jaw 600a has a front element, herein denoted by 601a, and a support element, denoted by 602a.

Support element 602a has a curved profile, preferably an arched profile similar to that of FIG. 4a. Support element 602a has a central rib 635 protruding, along the z axis, inwardly with respect to the space subtended by the arch. Preferably, rib 635 is positioned in the middle or central portion of the arch.

Each of the two opposite ends of the arch terminates with a lateral abutment or bracket 633, 634, preferably flat, protruding along the y axis inwardly with respect to the space subtended by the arch. In addition, each of lateral abutments 633, 634 houses a respective permanent magnet 661, 662. The position of permanent magnets 661 and 662 on the lateral abutments 633 and 634 is such that opposite poles are alternated. In other words, the sequence of opposite poles on lateral abutments 633, 634, along the y axis, is N, S, N, S or S, N, S, N.

Front element 601a has a curved profile, preferably an arched profile, most preferably with a radius of curvature higher than that of support element 602a.

Each of the two opposite ends of the arched profile of front element 601a terminates with a lateral abutment or bracket 623, 624, preferably flat, protruding along the y axis inwardly with respect to the space subtended by the arch. Front element 601a further comprises a rib 622, protruding along the z axis inwardly with respect to the space subtended by the arch of the front element 601a and preferably located in the middle or central portion of this arch. Moreover, rib 622 houses a permanent magnet 663, positioned so as its poles face homologous poles on the lateral abutments 633, 634 of support element 602a. In other words, the overall sequence of opposite poles on jaw 600a, along the y axis, is N, S, S, N, N, S or S, N, N, S, S, N.

Front element 601a and support element 602a are fixed one another along respective lateral abutments 623, 633 and 624, 634, representing the longitudinal edge portions of the two elements.

Figure 9A:
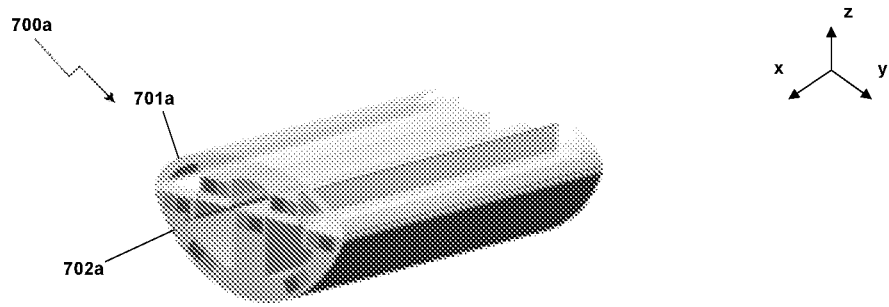
FIG. 9a is a perspective view of a jaw of a miniaturized grasper device according to a seventh embodiment of the invention.
Figure 9B:
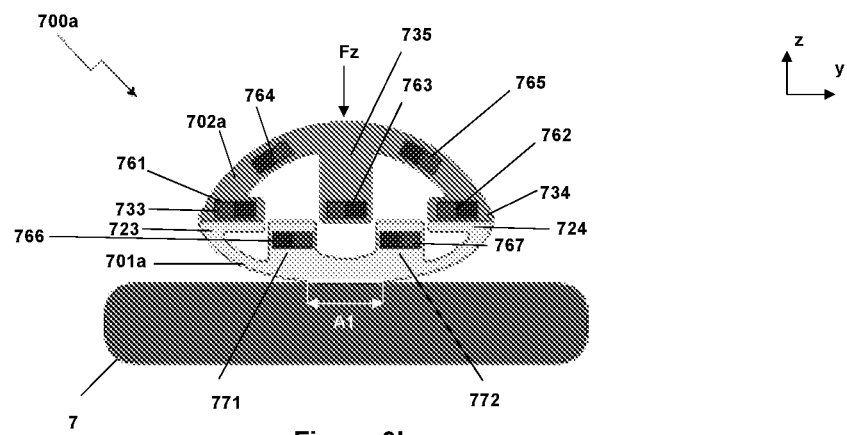
FIG. 9b is a schematic cross-section of a jaw of the miniaturized grasper device shown in FIG. 9a in an "unloaded" configuration.
Figure 9C:
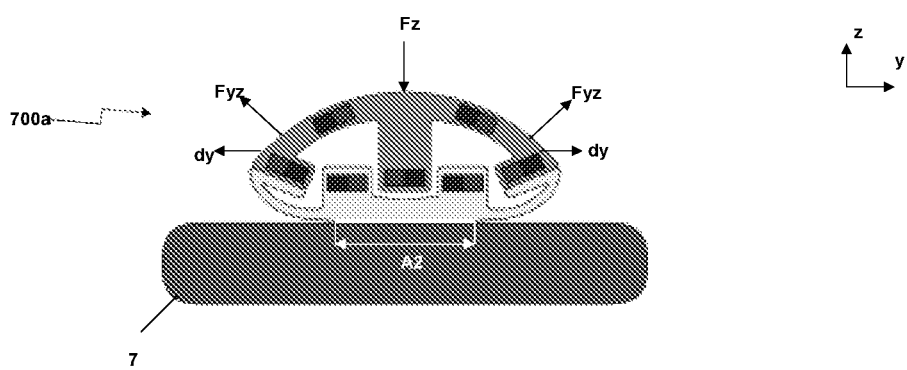
FIG. 9c is a schematic cross-section of a jaw of the miniaturized grasper device shown in FIG. 9a in a "bent", or deformed, configuration.

FIGS. 9a-9c depict another embodiment of the present invention and show a jaw denoted by 700a. Jaw 700a has a front element, herein denoted by 701a, and a support element, denoted by 702a.

Support element 702a has a configuration similar to that of FIG. 8a-8c and includes additional magnets. In particular, support element 702a has a curved profile, preferably an arched profile, comprising a rib 735 protruding, along the z axis, inwardly with respect to the space subtended by the arched profile. Preferably, rib 735 is positioned in the middle or central portion of the arch. Each of the two opposite ends of the arch terminates with a lateral abutment or bracket 733, 734, preferably flat, protruding along the y axis inwardly with respect to the space subtended by the arch. Permanent magnets 761 and 762 are housed within the lateral abutments 733, 734 and a permanent magnet 763 is housed within rib 735. Additional magnets 764 and 765 are housed in the lateral portions of the arched profile comprised therebetween according to a symmetrical arrangement. Permanent magnets 761 to 765 on the support element 702a are positioned so as opposite poles face each other.

Font element 701a has a curved profile, preferably an arched profile, most preferably with a radius of curvature higher than that of support element 702a. Front element 701a comprises two central ribs or protrusions 771 and 772, each housing a respective permanent magnet 766 and 767. Ribs 771 and 772 protrude, along the z axis, inwardly with respect to the space subtended by the arch and are preferably located aside with respect to rib 735 on support element 702a. In particular, permanent magnets 766 and 767 on the two ribs 771 and 772 are positioned so as their poles face the opposite pole of the permanent magnet located within the other rib.

Front element 701a further includes lateral abutments or brackets 723 and 724, along which it is fixedly coupled with the support element 702a. As for prior embodiments, lateral abutments 723, 724 and 733, 734 represent the longitudinal edge portions of the front and support element.

Figure 10A:
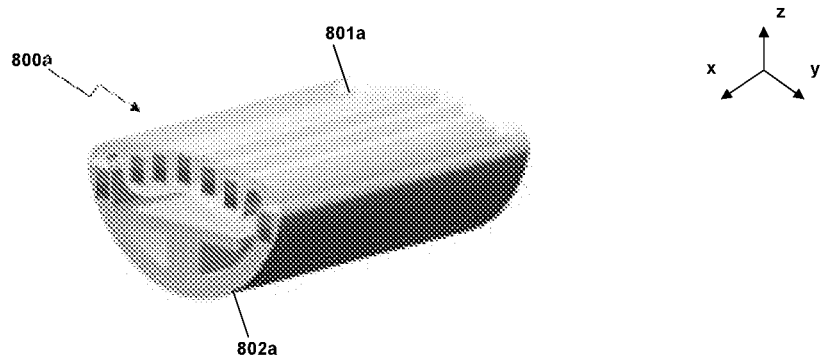
FIG. 10a is a perspective view of a jaw of a miniaturized grasper device according to an eighth embodiment of the invention.
Figure 10B:
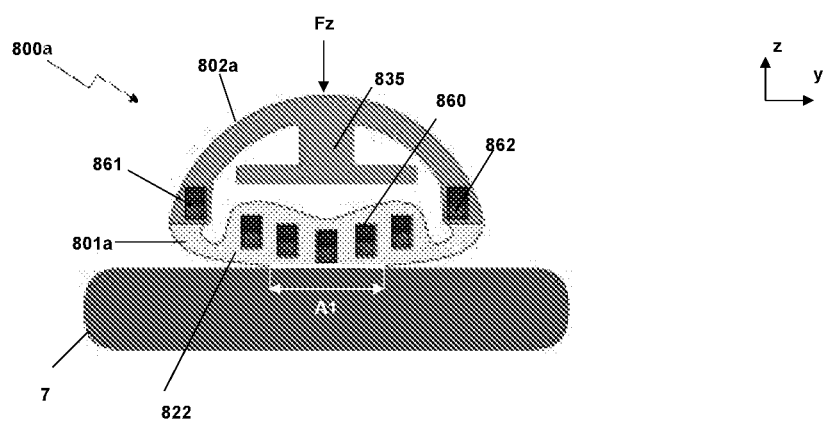
FIG. 10b is a schematic cross-section of a jaw of the miniaturized grasper device shown in FIG. 10a in an "unloaded" configuration.
Figure 10C:
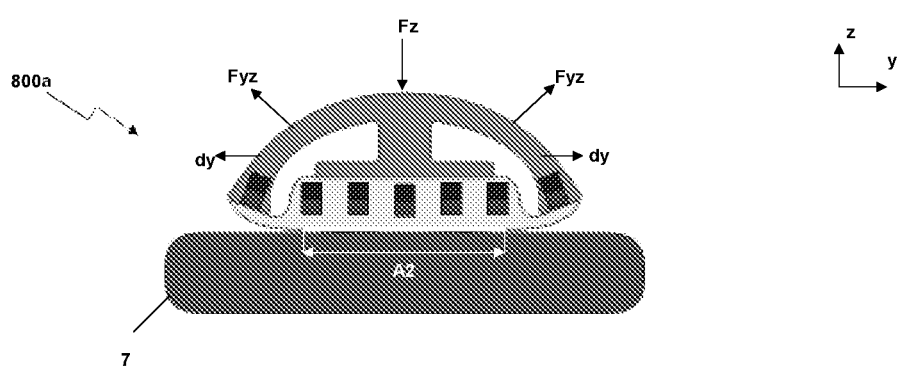
FIG. 10c is a schematic cross-section of a jaw of the miniaturized grasper device shown in FIG. 10a in a "bent", or deformed, configuration.

FIGS. 10a-10c depict another embodiment of the present invention and show a jaw denoted by 800a. Jaw 800a has a front element, herein denoted by 801a, and a support element, denoted by 802a.

Support element 802a has a curved profile, preferably an arched profile, and comprises a rib 835 protruding, along the z axis, inwardly with respect to the space subtended by the arch. Preferably rib 835 is positioned in the middle or central portion of the arch and is T-shaped in cross-section.

Front element 801a has a curved profile, preferably an arched profile, most preferably with a radius of curvature higher than that of support element 802a. In particular, front element 801a has a bulge 822, preferably in the middle or central position of the arch. A plurality of permanent magnets, globally denoted by 860, is housed within bulge 822, in particular five magnets in the present example. Other two permanent magnets 861, 862 are located within the two opposite ends of the arch of the support element 802a. All the permanent magnets are positioned along the z axis in such a way that all the similar poles have the same orientation. In other words, all the south poles or all the north ones face the item 7 to be grasped.

Generally speaking, in specific embodiments the front element of the grasper device has a longitudinal length of about 10 mm ($L_x$), a transverse dimension ($L_y$) of about 8 mm and a thickness of about 1.5 mm.

In particular embodiments, the support element has a typical longitudinal length of about 10 mm ($L_x$), a transverse dimension ($L_y$) of about 8 mm and a thickness of about 0.4 mm.

On one or both jaws of the device according to the invention, there could be further provided sensing capabilities, such as by on-board sensors and related feedback modalities, in particular distally integrated visual feedback element like LED arrays.

The present invention has been described with reference to preferred embodiments. However, it will be understood that variations and/or modifications can be brought to the grasper device according to the present invention without thereby departing from the scope of the invention as defined in the following claims.

The invention claimed is:

1. A grasper device adapted for minimally-invasive surgery, said grasper device is configured to be attached to a support tool, the grasper device comprising two jaws, each of said two jaws having:
   an elastically-deformable front element, which, in operation, is in contact with an item to be grasped; and
   an elastically-deformable back support element fixed to the elastically-deformable front element and configured to receive a grasping force ($F_z$), said elastically-deformable back support element has a higher modulus of elasticity than the elastically-deformable front element, being less elastically-deformable,
wherein said elastically-deformable front element and said elastically-deformable back support element each develop according to a main longitudinal direction (x) and are fixed one another along respective longitudinal edge portions so as to define a tubular hollow structure,
the overall arrangement being such that when the grasping force ($F_z$) is applied to said elastically-deformable back support element, it deforms and transmits the grasping force to the front element which, in turn, deforms,
both the elastically-deformable front element and the elastically-deformable back support element deforming in a main deforming transverse direction (y) that is orthogonal to said main longitudinal direction (x) and to the grasping force ($F_z$).

2. The grasper device according to claim 1, wherein each jaw of said two jaws has, in cross-section, a symmetrical structure with respect to an axis of symmetry (z) orthogonal to said main deforming transverse direction (y).

3. The grasper device according to claim 1, wherein the elastically-deformable front element has a curved, or arched, profile.

4. The grasper device according to claim 1, wherein the elastically-deformable front element has a substantially bilobed profile made by two symmetric bilobed coves arranged side by side along said main deforming transverse direction (y).

5. The grasper device according to claim 1, wherein the elastically-deformable front element comprises lateral abutments extending inwardly or outwardly with respect to an inner space subtended by the elastically-deformable front element, at which lateral abutments the elastically-deformable front element is connected to the elastically-deformable back support element.

6. The grasper device according to claim 1, wherein the elastically-deformable front element comprises a rib or a bulge protruding inwardly with respect to an inner space subtended by a profile of the elastically-deformable front element.

7. The grasper device according to claim 1, wherein the elastically-deformable back support element has a curved, or arched, profile.

8. The grasper device according to claim 1, wherein the elastically-deformable back support element comprises a rib protruding inwardly with respect to an inner space subtended by the support element.

9. The grasper device according to claim 8, wherein said rib has, in cross-section, a straight profile, a tapered profile narrowing towards the front element or T-shaped profile.

10. The grasper device according to claim 1, wherein the elastically-deformable back support element comprises lateral abutments extending inwardly with respect to an inner space subtended by the elastically-deformable back support element, at said lateral abutments the elastically-deformable front element is connected to the elastically-deformable back support element.

11. The grasper device according to claim 1, comprising one or more fillers, housed in said tubular hollow structure.

12. The grasper device according to claim 11, wherein said one or more fillers are sliding elements.

13. The grasper device according to claim 1, comprising at least a couple of magnetic elements housed within the elastically-deformable front element and/or the elastically-deformable back support element, the overall arrangement being such that, upon deformation of the elastically-deformable front element and/or the elastically-deformable back support element, the magnetic elements relative position changes and repulsive forces between facing magnet poles are induced.

14. The grasper device according to claim 1, wherein the elastically-deformable front element is made of a silicon rubber material.

15. The grasper device according to claim 1, wherein the elastically-deformable back support element is made of thermoplastic materials or of super-elastic alloys.

16. A surgical tool for minimally-invasive surgery, comprising a grasper device according to claim 1.

17. The grasper device according to claim 1, wherein the elastically-deformable front element comprises a rib or a bulge protruding inwardly with respect to an inner space subtended by a profile of the elastically-deformable front element and arranged at a central region thereof.

18. The grasper device according to claim 1, wherein the elastically-deformable black support element comprises a rib protruding inwardly with respect to an inner space subtended by the support element and arranged at a central region thereof.

19. The grasper device according to claim 11, wherein the one or more fillers are deformable.

* * * * *